US00PP37096P2

(12) United States Plant Patent
Hansoti

(10) Patent No.: US PP37,096 P2
(45) Date of Patent: Nov. 11, 2025

(54) ***SANSEVIERIA* PLANT NAMED 'HANSOTI59'**

(50) Latin Name: *Sansevieria trifasciata*
Varietal Denomination: HANSOTI59

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/000,680

(22) Filed: Dec. 23, 2024

(51) Int. Cl.
*A01H 5/12* (2018.01)
*A01H 6/12* (2018.01)

(52) U.S. Cl.
USPC ..... Plt./382

(58) Field of Classification Search
USPC ..... Plt./382
CPC ..... A01H 5/12; A01H 5/00; A01H 6/12
See application file for complete search history.

(56) References Cited

PUBLICATIONS

National Parks Flora & Fauna Web retrieved on Mar. 17, 2025 at https://www.nparks.gov.sg/florafaunaweb/flora/4/6/4668, 5 pp. (Year: 2025).*

* cited by examiner

*Primary Examiner* — June Hwu

(57) ABSTRACT

A new and distinct cultivar of *Sansevieria* plant named 'HANSOTI59' is disclosed, characterized by foliage variegation in the form of linear bands and streaks of different grey-greens and creams along the length of the leaf, a dark green leaf border and a golden yellow suffusion towards the base of the leaf. Unusually upright, relatively narrow leaves give a particularly vertically oriented narrow rosette of greyish-green to cream-streaked leaves. Unique slow changing of the variegation pattern and color of new leaves as more leaves emerge from an older plant to give a creamier look as the plant ages. The new cultivar can be classified in the Compact *Sansevieria* Group. The new variety is a *Sansevieria*, typically produced as an ornamental plant.

12 Drawing Sheets

Latin name of the genus and species: *Sansevieria trifasciata.*

Variety denomination: 'HANSOTI59'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI59'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI59' was discovered and selected by the inventor, Ashish Hansoti, as a naturally-occurring mutation from an aberrant *Sansevieria trifasciata* 'Black Moon' (an unpatented cultivar selected and grown by the Inventor) in 2018, at a nursery in Village Vangani, District Thane, Maharashtra State in Western India.

Asexual reproduction in good numbers of the new, relatively stabilised *Sansevieria* cultivar 'HANSOTI59' by vegetative cuttings was started March-April 2020 at Village Asle, District Satara, Maharashtra State in Western India and it was seen that, after a few more rounds of discarding of off-types, the distinctive combination of characteristics of the new cultivar reproduced true to type as long as the propagation was done through side shoots (basal suckers) originating from the base of the parent plant. Thus, it can be said that the new cultivar reproduces true to type through side shoots (basal suckers)

BRIEF SUMMARY OF THE INVENTION

The following traits have been repeatedly observed and are determined to be unique characteristics of 'HANSOTI59', which in combination distinguish this *Sansevieria* as a new and distinct cultivar:

1. Foliage variegation in the form of linear bands and streaks of different grey-greens and creams along the length of the leaf, a dark green leaf border and a golden yellow suffusion towards the base of the leaf.
2. Unusually upright, relatively narrow leaves giving a particularly vertically oriented narrow rosette of greyish-green to cream-streaked leaves. Such a vertical rosette makes for a potted plant that's easier to handle and easier to pack.
3. Slowly changing of the variegation pattern and color of new leaves as more leaves emerge from an older plant to give a creamier look as the plant ages. Overall 'Hansoti59' is one of the more colorful *Sansevieria* hybrids known to the inventor.
4. Changing color and variegation pattern of newly emerging leaves with increasing plant age-leaves in a young plant (3-5 months from rooted liner) are typically grey-green with a thin 1 to 3 mm green outer edge and a white to cream inner border of 1 to 3 mm width. Basal $1/3^{rd}$ of each leaf is suffused with yellow while the top $2/3^{rd}$ lacks this suffusion and is more grey-green. As the plant ages and matures, the new leaves emerge with increasing amounts of yellow-cream colored variegation, with an enhanced dark green border varying from 1 to 10 mm wide and a central band of green streaks overlaid with yellowish cream to varying degrees. This variability in the plant coloring is standard and stable in this cultivar and all plants in a bench of 'Hansoti59' exhibit this variation and change in color.

5. At 20-25 cm plant height overall, this is one of the cultivars with shorter leaves but still exhibits average height due to the straight leaves and their vertical orientation, an unusual trait amongst the *Sansevieria trifasciata* cultivars nominated as "Compact *Sansevieria* Group".
6. Ready to sell, 3-month (from rooted liner) old plants have 7-9 leaves per plant which is relatively high compared to other *Sansevieria* in the Compact Group, which at this age have 4-6 leaves. This gives a more bushy, full plant compared to other *Sansevieria* in the Compact Group.

The new variety 'HANSOTI59' is considered a variety of *Sansevieria* in the group denominated as the "Compact *Sansevieria* Group". The new variety presents an average of 7 to 9 leaves per plant when it reaches its saleable size (between 3 to 4 months from rooted liner). The new variety has a semi-erect growth habit and the entire plant can reach a height ranging between 20 and 25 cm. The leaves are of medium width (4 to 5 cm) measured at the widest part of the mature leaf under good growing conditions) and broad-lanceolate with a firm, waxy texture. The blades are thick or fleshy and slightly wavy. This variety also has an inverted triangle shape like most *Sansevieria* of the Compact Group but the whole rosette is narrower and more vertical rather than spreading compared to other cultivars.

The new variety is moderately drought tolerant and adapts well to conditions of bright light and heavy shade (exterior and interior).

Describing the leaf is more than usually difficult as the leaves in young plants (3-6 months old) are significantly different compared to leaves that emerge from the same plant subsequently, when the plant is older than 4-5 months (from rooted liner). To a large extent the leaves that will be seen in commercial cultivation and sale of this cultivar will be the grey-green leaves of younger plants.

The overall impression is of a grey-green leaf with longitudinal striations in light grey and grey-green. A closer inspection reveals a white border along the outer edge and a dark green line along the outermost edge of the leaf.

The dark green edge is close to RHS Green 139A and the white border is similar to White 155B. The longitudinal lines and striations are similar to Greyed-Green N189B.

Another interesting aspect is the suffusion of yellow in the full lower ⅓$^{rd}$ to ½ of the leaf. This suffusion is close to RHS Yellow-Green 145A and is seen in leaves from plants of all ages.

Very young emerging shoots are obviously much paler with a whitish-cream color similar to but even lighter than RHS White 155A on inside of leaf and similar to Gray-Green 191C or 191D on the outside and a very pale background color of Yellow 2C. Marginal band is brighter green.

As the plant ages, the new emerging leaves change their variegation pattern substantially. The green edge becomes a green border 2 to 10 mm wide, its color close to RHS Green 139A. Within the two borders on either side of the leaf the amount of creamy-yellow increases substantially and can be seen as bands from 2 to 10 mm wide. These bands keep increasing in width till they almost cover the whole width of the leaf.

The lines of grey-green (close to RHS Greyed-Green N189B) persist for a few leaves but are more and more invaded by creamy-yellow streaks. Eventually, the most mature leaves are almost entirely creamy-yellow (Close to Yellow 3C and 4B) with just a few grey-green streaks in the centre, mostly veiled by a layer of cream epidermis.

Backside of the leaves is similarly colored with wide central darker band and thinned marginal bands. However, usually the whole of the backside of the leaf is more uniform due to thicker overlying layer of greyish cream (RHS Greyed-Green 189B) so that the darker vertical bands (Green N189B) are less distinct that on the front or top of the leaf.

PARENTAL COMPARISON

Plants of the new *Sansevieria* 'HANSOTI59' are similar to plants of the parental cultivar, however, 'HANSOTI59' differs in the characteristics described in Table I. Plants measured were approximately 6 months of age, unless otherwise noted.

TABLE I

Comparison of Parental & the New variety 'Hansoti59'

| | Characteristic | Parent 'Black Moon' Special Selection | New cv 'Hansoti59' |
|---|---|---|---|
| 1. | Overall Color | Dark green with prominent horizontal striations (typical of *S. trifasciata* cultivars) & a single stripe of white on one leaf, appearance consistent at any age. The original cultivar 'Black Moon' itself is entirely green. | Creamy-grey with grey-green bands of various widths giving a bright, light grey variegated appearance (2 month to 4 months). |
| 2. | Variegation Pattern | No variegation at any stage of maturity. | Complex variegation giving, in a young plant(around 2 months), leaves of grey-green color and bright cream leaves in older plants(around 6 months). |
| 3. | Border | No border stripe along leaf edge at any age of maturity. | Dark green border 1-5 mm wide and a white border inside this green line of 1-3 mm width. Border present at 2 months and older.) |
| 4. | Central variegation | No central variegation except a white stripe 7-8 mm wide on one leaf in this particular mother plant at any age. | Light grey-green striations cover most of the centre of the leaf (2 months). As plant ages creamy-yellow striations and bands start to appear around 4 months and increase significantly until 12 month old plants have significant creamy yellow coloration. At 2 years this creamy yellow coloration predominates_and leaves in oldest plants can be almost entirely creamy-yellow. |
| 5. | Leaf shape | Broad, stiff lanceolate leaf in a wide rosette. | Narrower leaves, straight and more vertically held. |
| 6. | Vigor | Very vigorous | Somewhat less vigorous but still a strong grower. |

A special selection from the variety 'Black Moon' gave rise to the variety 'Hansoti59'. 'Black Moon', being almost entirely dark green, shows stronger vigor than 'Hansoti59' but has fewer leaves per plant (5-7), with a broader leaf with an average leaf width of 8-10 cm (measured in the middle of the mature leaf.) The growth habit is semi-erect and presents its leaves in a wide rosette. The entire plant can reach a size from 25-30 cm. The plant has, as for 'Hansoti59', an inverted triangle shape. The leaves are broad lanceolate with a waxy texture.

Overall, the plants of 'Black Moon' look dark green with no variegation but with prominent transverse banding so common in *S. trifasciata* cultivars while the specific, select parent plant had a single white stripe along one leaf. 'Hansoti59' presents very differently, as a variegated, much brighter, highly colored plant with stripes of creamy-grey, a wide green central band with greyish overlay and a brighter green, thinner marginal band and a suffusion of yellow on approximately the lower ⅓$^{rd}$ of the leaf. The overall bright coloration is striking and very unique amongst *Sansevieria*, most of them being much less colorful.

COMMERCIAL COMPARATOR

Plants of the new *Sansevieria* 'HANSOTI59' are similar to the commercial variety *Sansevieria* 'Frozen', U.S. Plant Pat. No. 29,345. However, 'HANSOTI59' differs in the characteristics described in Table II. Plants measured were approximately 6 months of age, unless otherwise noted.

TABLE II

Comparison of known, patented variety 'Frozen' & the new variety 'Hansoti59'

| | Characteristic | Comparable Cultivar 'Frozen' | New cv 'Hansoti59' |
|---|---|---|---|
| 1. | Leaf size | Up to 25-30 cm | 20 to 25 cm long |
| 2. | Number of leaves | 5 to 7 leaves | 8 to 10 leaves per plant (More leaves) |
| 3. | Leaf shape & width | Leaves unusually broad compared to most other "Compact *Sansevieria* Group" cultivars | Leaves unusually narrow compared to most other "Compact *Sansevieria* Group" cultivars |
| 4. | Variegation Pattern | Transverse greyed-green and dark green . banding | Highly variegated - Grey green stripes and striations along length of leaf on cream background 2 to 4 months), with whole leaf turning cream in older plants(6 months and older). |
| 5. | Border variegation | None | Variable, ranging from thin cream line to broader green and cream band. In leaves on older plants(12 months and older) can be entirely cream. |
| 6. | Central Variegation | No variegation - leaves are different shades of green, with green lines and horizontal striations typical in *S. trifasciata* but no variegation. | Broad grey-green band with an overlay of cream, darker grey-green striations interspersed with cream lines and bands |
| 7. | Changing leaf pattern | Leaf pattern and color of a particular leaf changes slightly with age but overall, leaves are always the same. | Variegation pattern/color of individual leaf does not change but new leaves are different in older plants(6 months and older) cf. to leaves emerging in young plants. |
| 8. | Leaf Cuttings | Comes true from leaf cuttings - adventitious shoots from leaves are identical to mother plants. | Does not come true from leaf cuttings - leaf cuttings give plain green shoots. |

BRIEF DESCRIPTION OF THE PHOTOGRAPHS

The accompanying photographs illustrate the overall appearance of the new *Sansevieria* cultivar. 'HANSOTI59' showing the colors as true as is reasonably possible with colored reproductions of this type. Colors in the photographs may differ slightly from the color value cited in the detailed botanical description which accurately describe the color of 'HANSOTI59'.

These pictures illustrate the plant form which is the unique characteristic of 'HANSOTI59' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

FIG. 1: Shows an old photo of the mother plant (a selection from the old cultivar, *S. trifasciata* 'Black Moon') showing the leaf with a single white stripe and the first aberrant side shoot which was selected as 'Hansoti59'. The mother plant is no longer in cultivation so contemporary photos are not possible.

FIG. 2, FIG. 3 and FIG. 4 show a saleable size plant of *Sansevieria* 'Hansoti59' in a 12 cm diameter pot at about 2.5 months old from various angles. The photos illustrate top as well as bottom of leaves and the leaf arrangement. FIG. 2 illustrates a view of a plant of 'Hansoti59' from about a 45 degree angle from the top. FIG. 3 illustrates the rather vertical leaf phyllotaxy.

Figure 1:
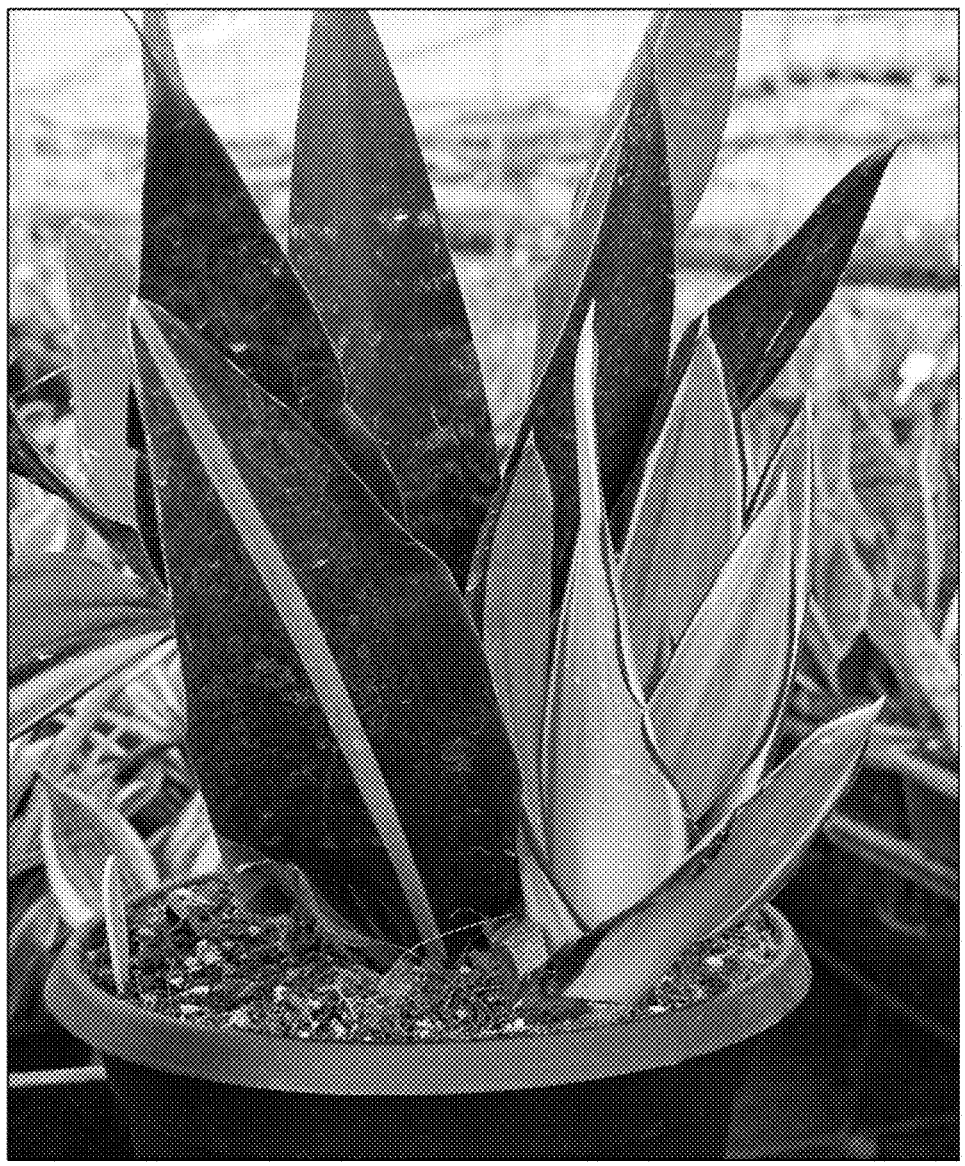
Figure 2:
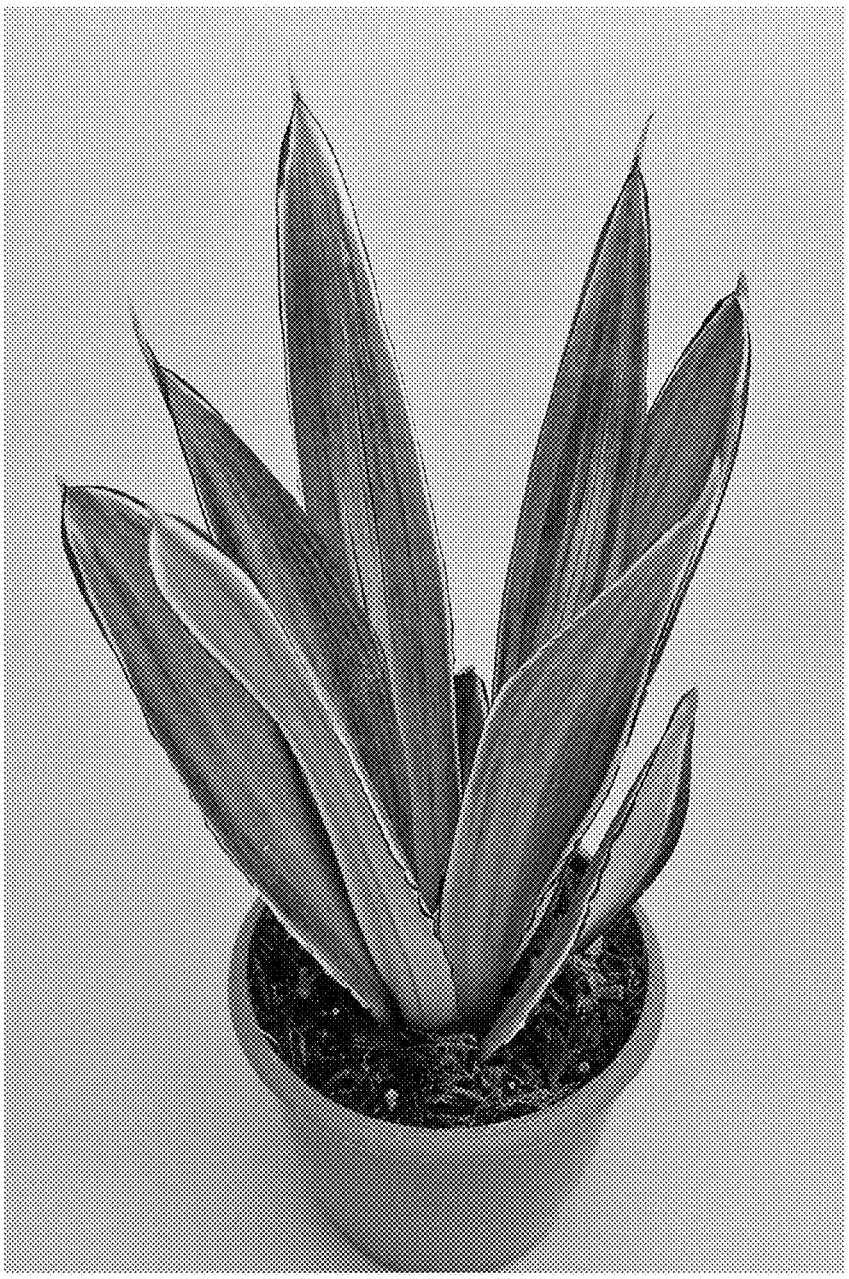
Figure 3:
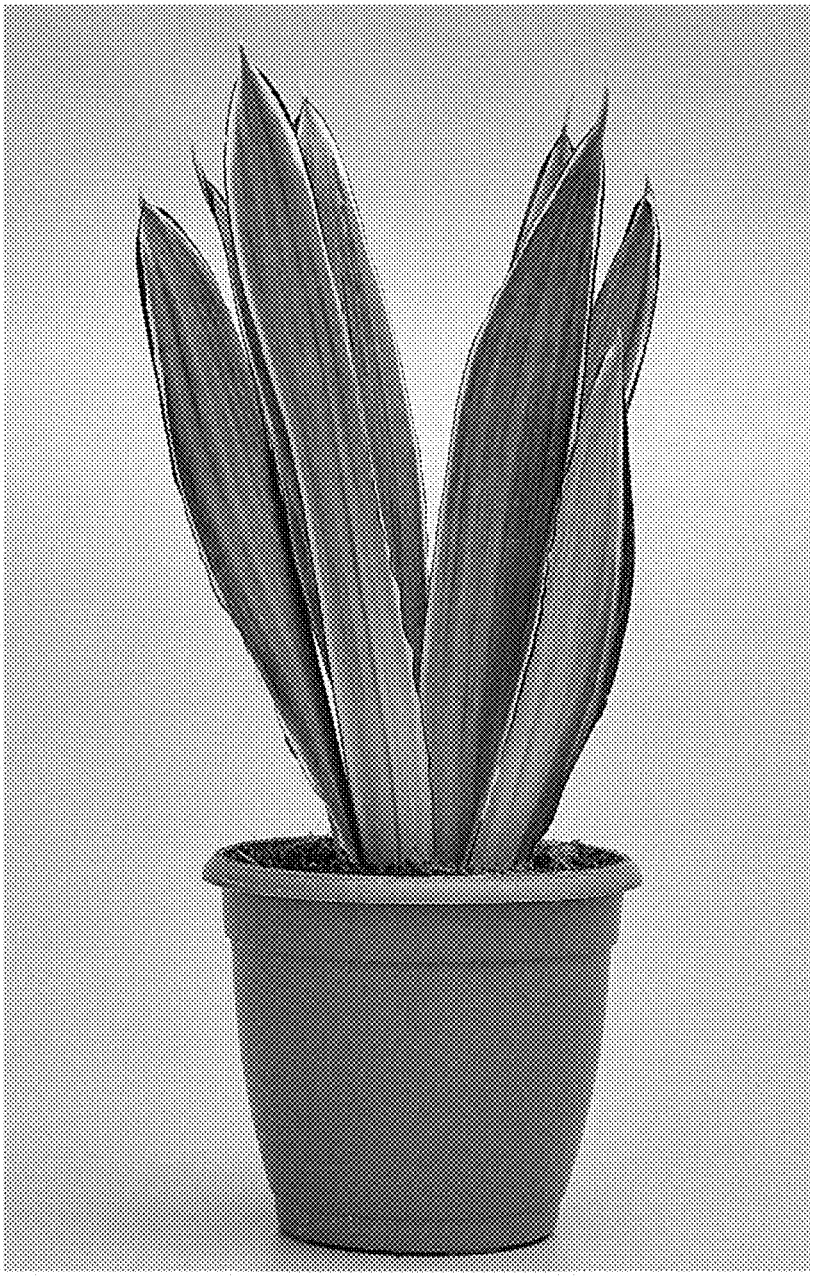
Figure 4:
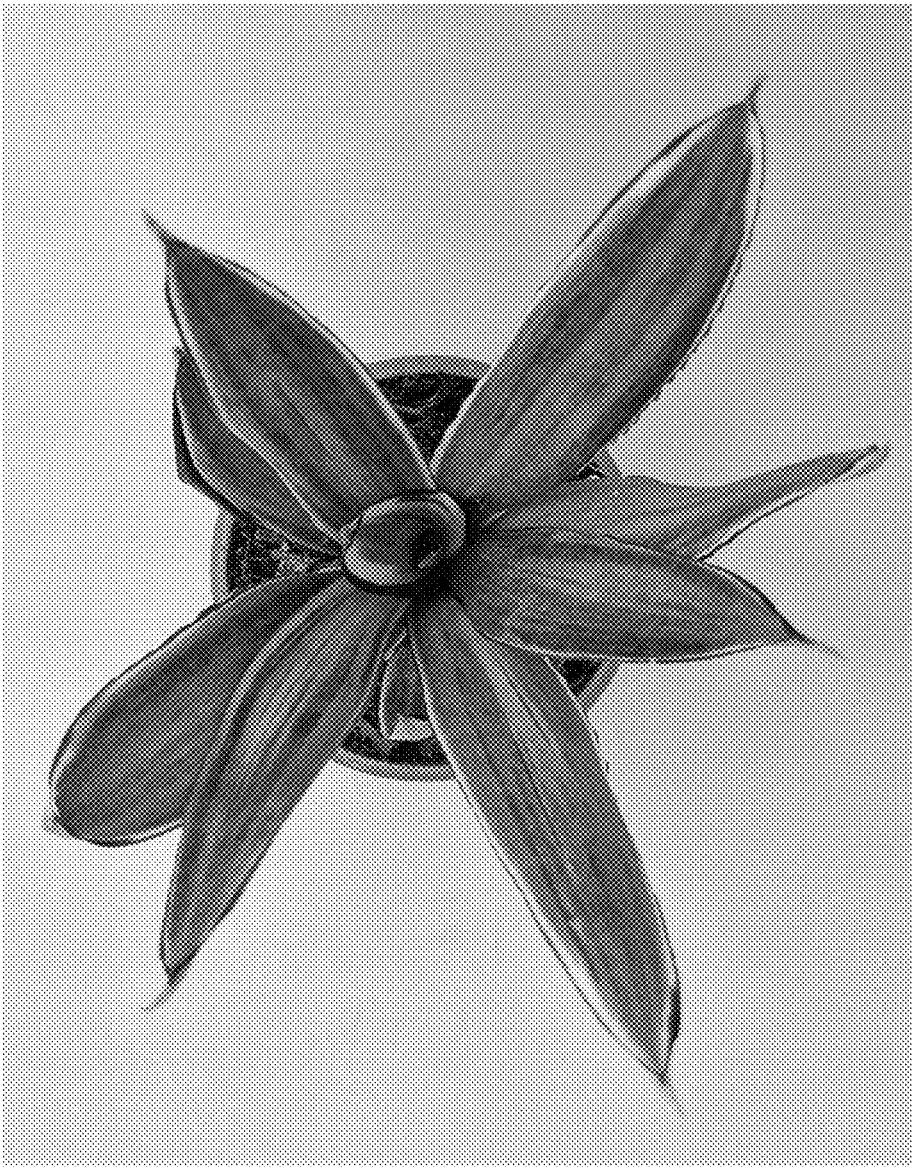
FIG. 4, illustrates a view of 'Hansoti59' directly from the top of the pot showing the yellow effusion on the lower third of each leaf. This plant is approximately 2.5 years old.
Figure 5:
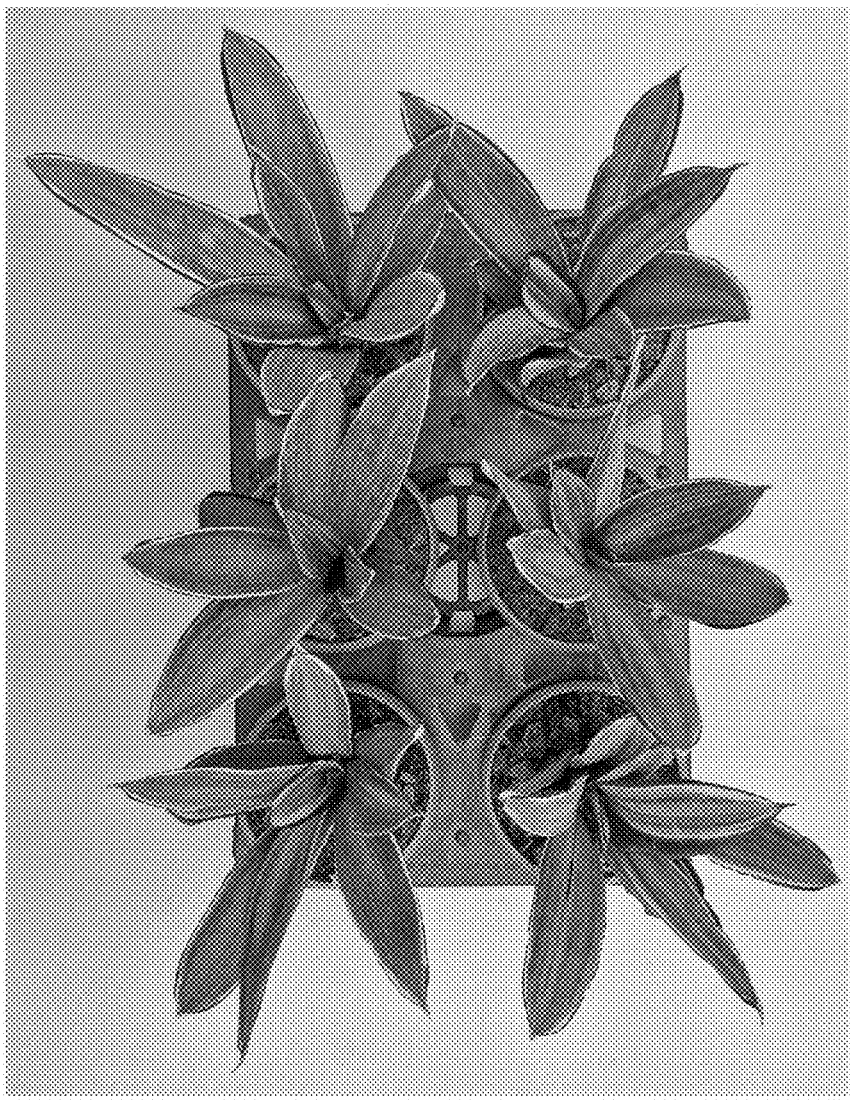
FIG. 5 is a top down view of 6 plants of 'Hansoti59' at about 2 months of age, showing uniformity across multiple plants.
Figure 6:
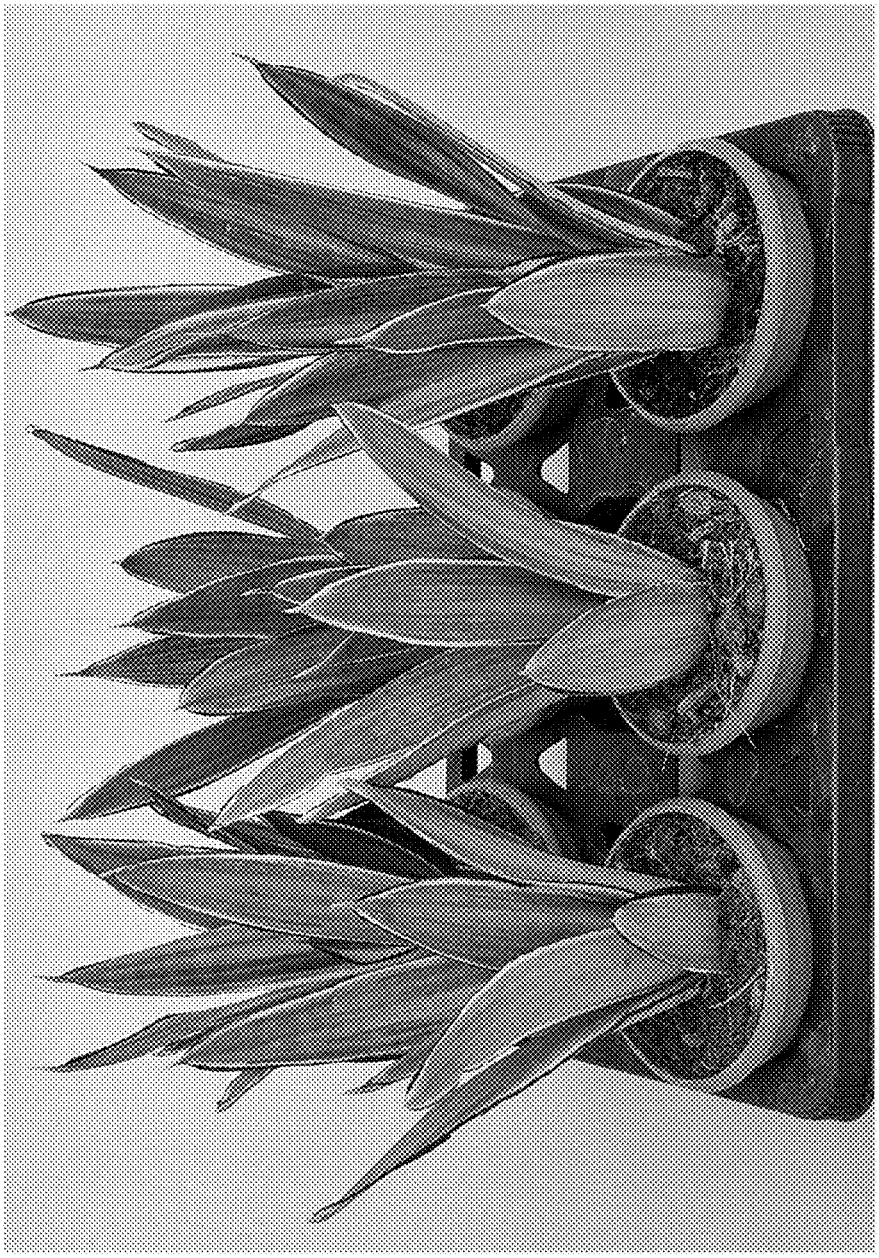
FIG. 6 is a view taken from an angle of about 45 degrees from the top of 6 plants of 'Hansoti59' at about 2 months of age, showing uniformity across multiple plants.
Figure 7:
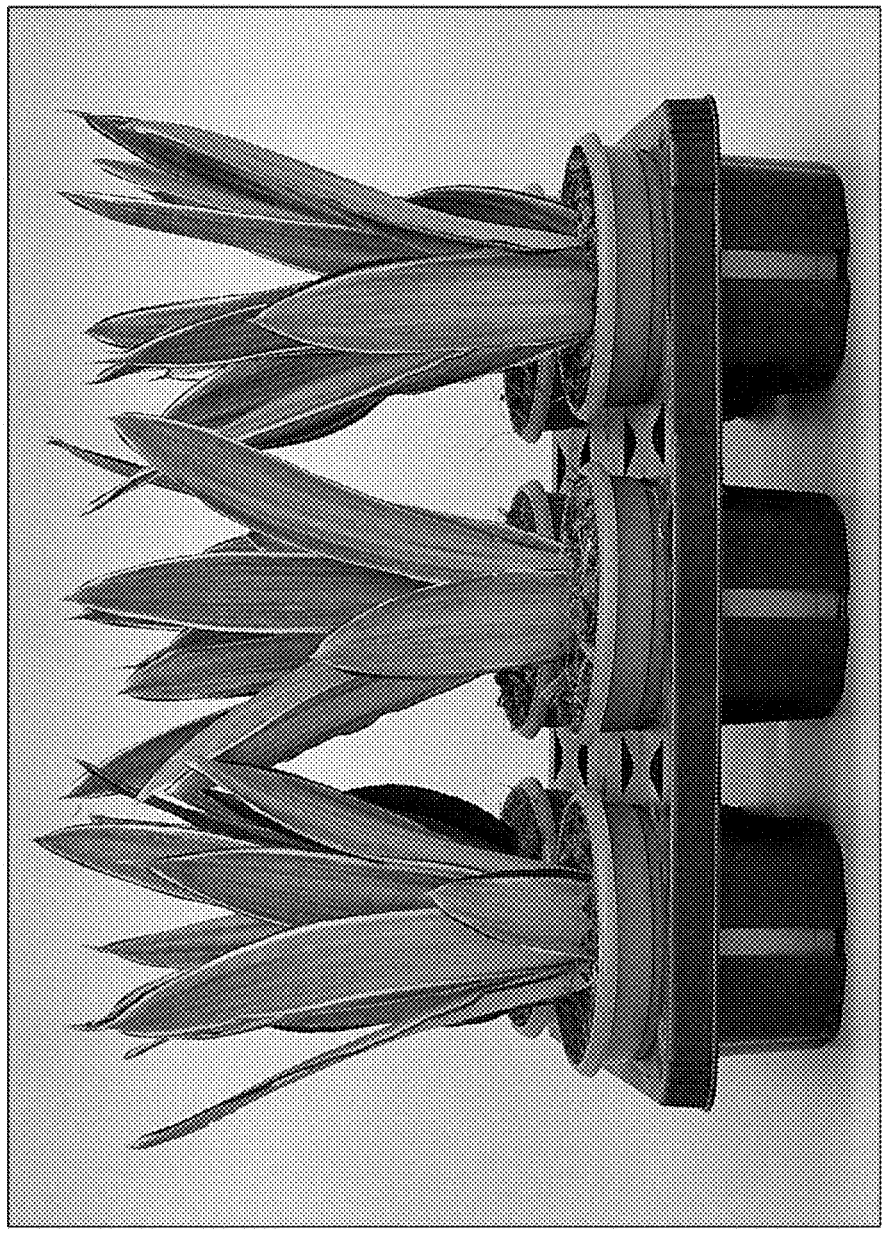
FIG. 7 is a side view of 6 plants of 'Hansoti59' at about 2 months of age, showing uniformity across multiple plants.
Figure 8:
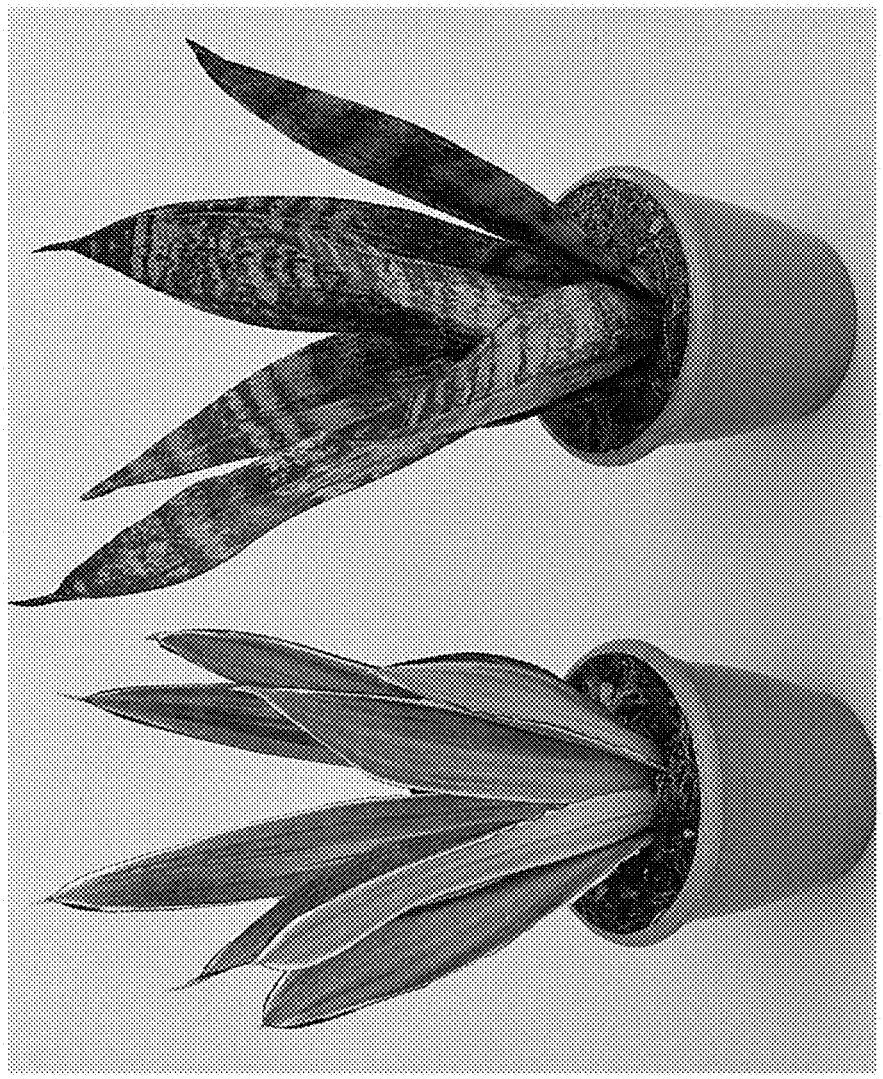

FIG. 8: Shows a plant of 'Hansoti59' (left side) next to a plant of a comparable cultivar *S. trifasciata* 'Frozen' (right side) to illustrate the similarities and differences.

Figure 9:
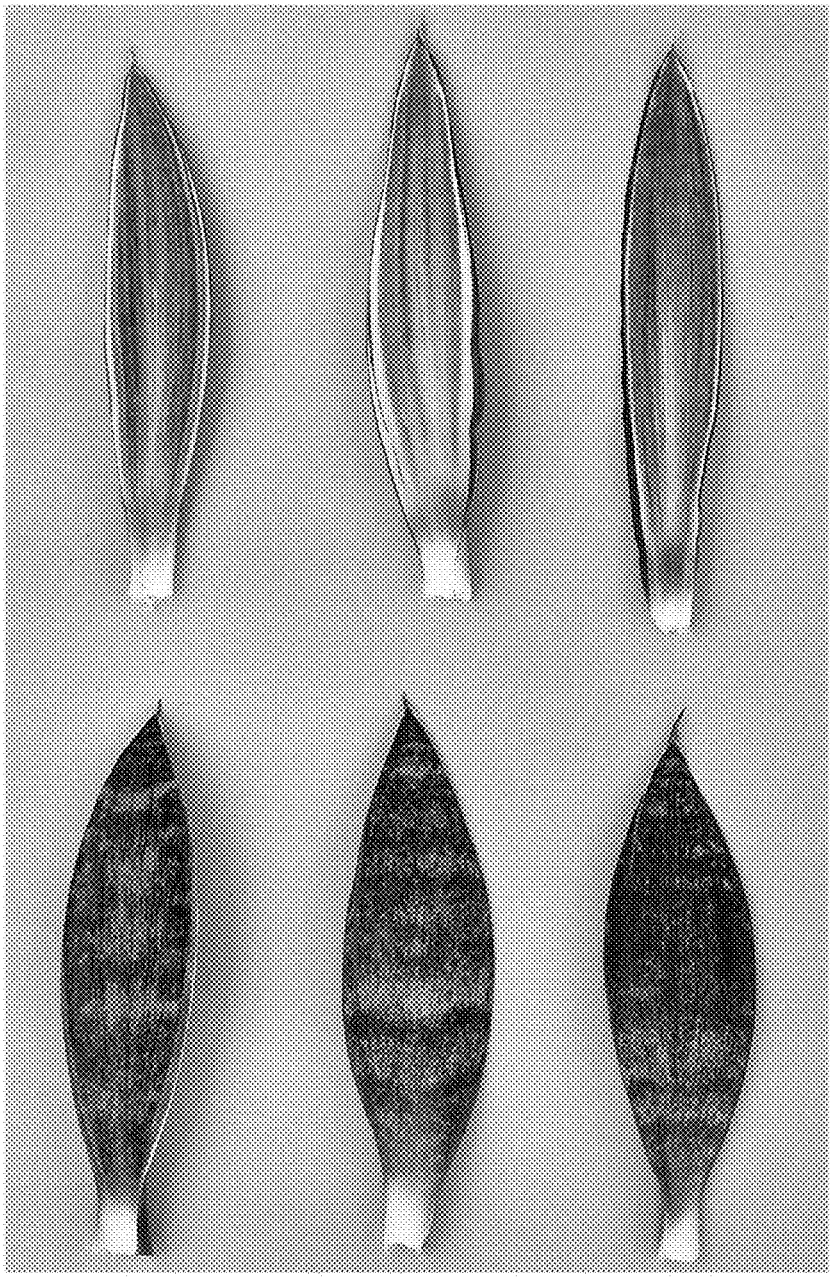

FIG. 9: Shows individual leaves (adaxial surface) of 'Hansoti59' (top row) and the comparable cultivar *S. trifasciata* 'Frozen' (bottom row) side by side clearly illustrating the differences in variegation pattern and colors of the two cultivars.

Figure 10:
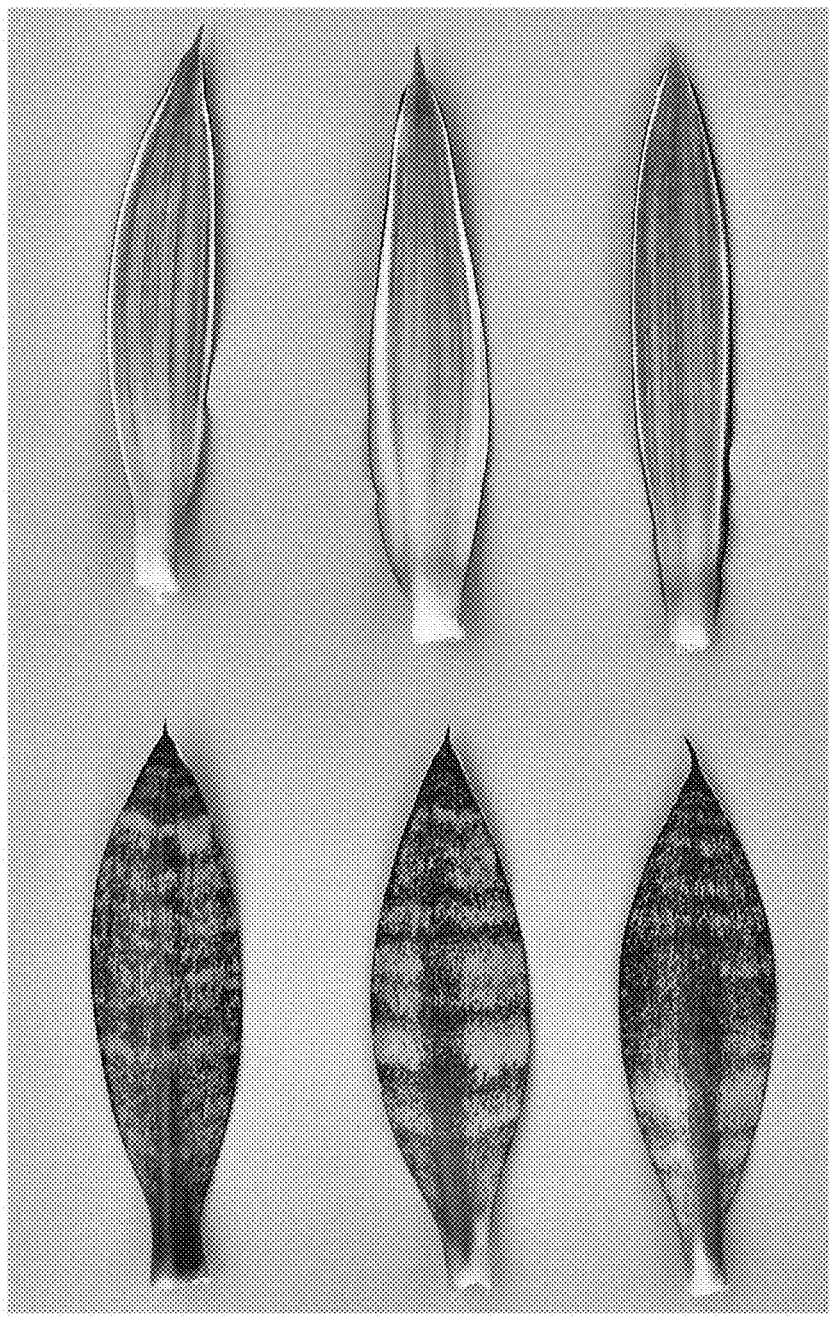

FIG. 10: Shows individual leaves (abaxial surface) of 'Hansoti59' (top row) and the comparable cultivar *S. trifasciata* 'Frozen' (bottom row) side by side clearly illustrating the differences in variegation pattern and colors of the two cultivars.

Figure 11:
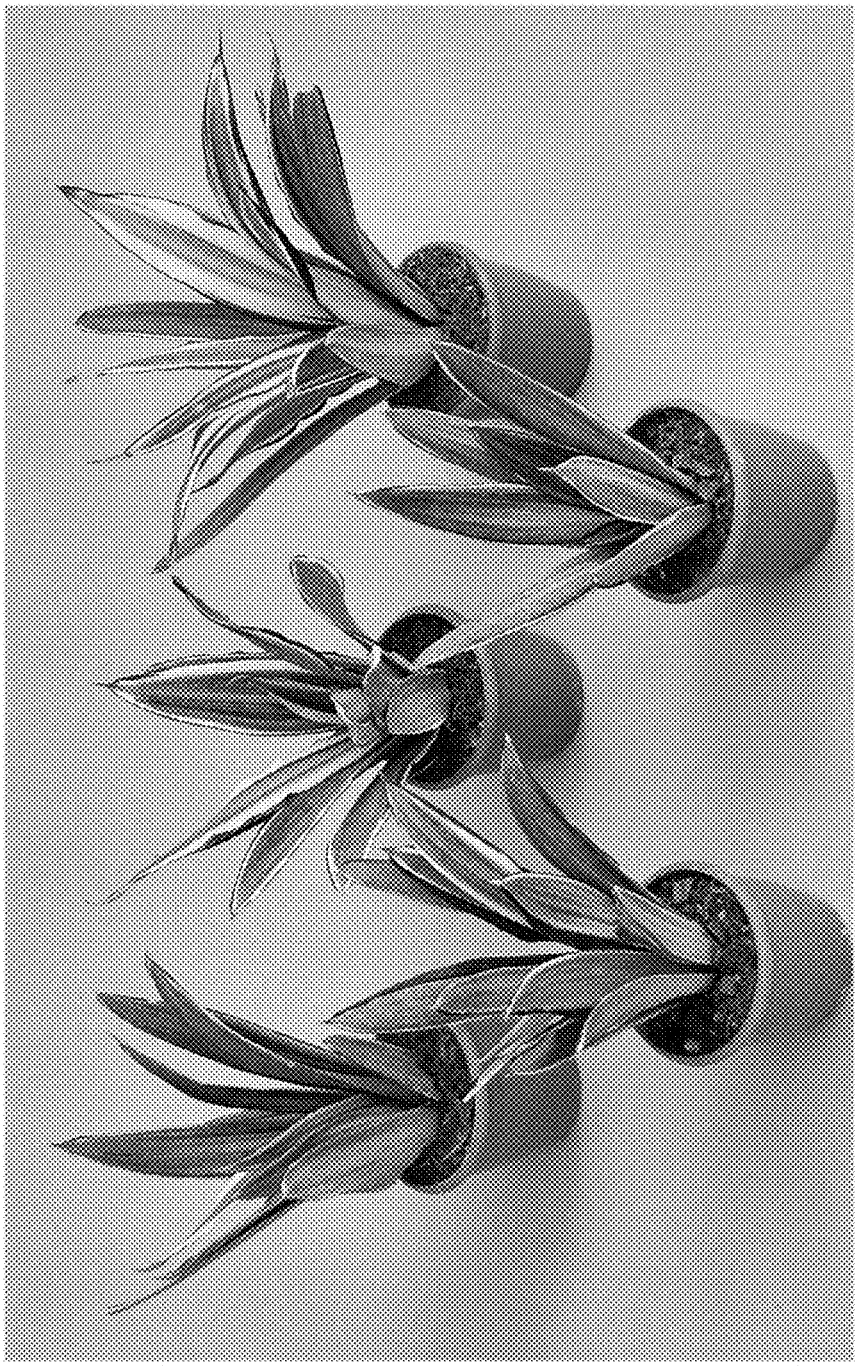

FIG. 11: illustrates the variegation color change with age, showing 5 plants of 'Hansoti59' at different ages from 2.5 moths to 2 years. The bottom row, left side is a plant of 2.5 months old, bottom row right wide is a 4 month old plant. The top row, left side is a 10 month old plant, center 12 month old plant and the right side top row is a 2 year old plant. Emerging leaves get brighter cream variegation as they emerge from older plants. Leaves also spread out a little. This change is a standard and consistent characteristic across all plants of 'Hansoti59'.

Figure 12:
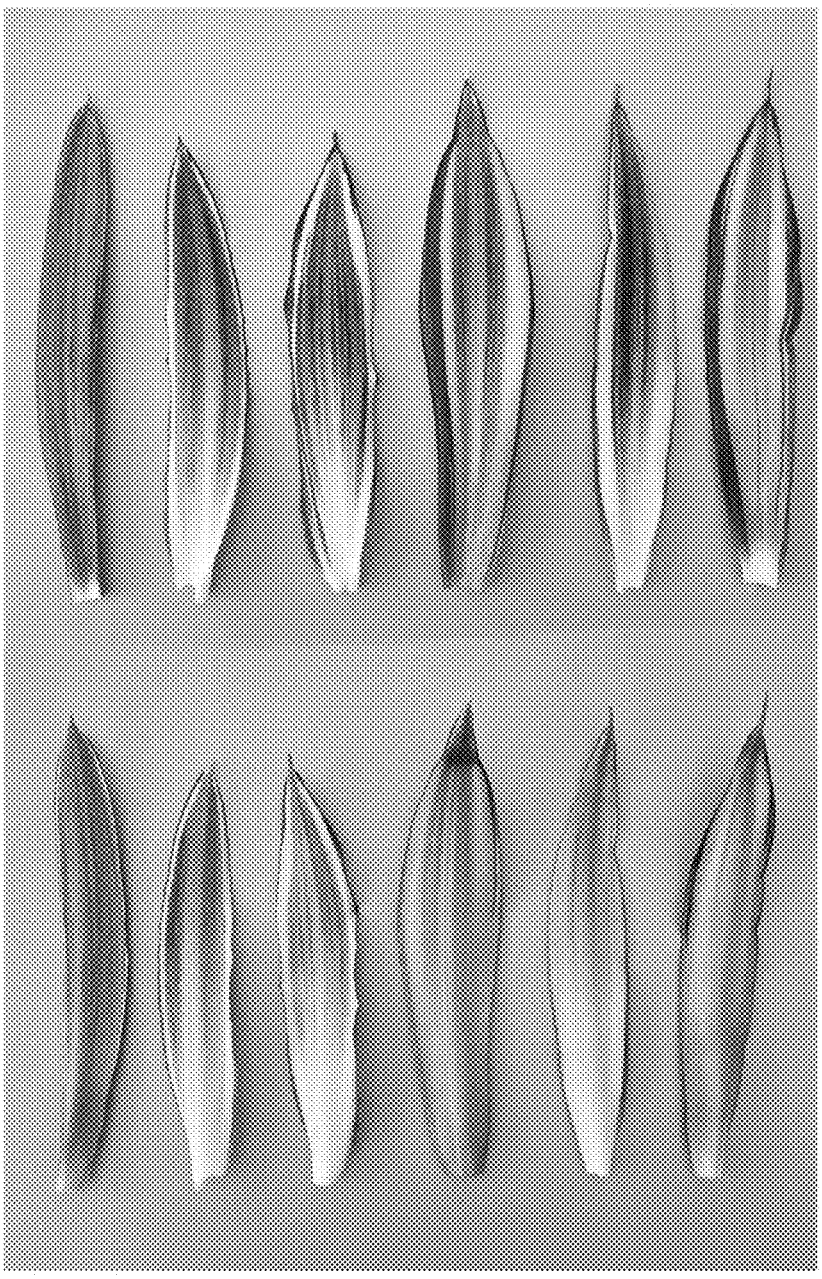

FIG. 12 shows a range of variegation pattern in individual leaves as plant ages. These are all from one plant at approximately 2.5 years old. Progressively older leaves showing how new leaves emerge with substantial change in variegation pattern and color; old leaf on right (which emerged when the plant was young) and progressively newer leaves as we go left (emerging from an older plant). Adaxial surfaces on top and abaxial surfaces of the same leaves in bottom row.

DETAILED BOTANICAL DESCRIPTION

The new *Sansevieria* 'HANSOTI59' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI59' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertiliser of 13:11:11 Type 360-days release at 1 kilo/cubic meter of media, constant liquid feed at approximately 100 ppm N, 30 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Color Chart (R.H.S.), (April 2007) except where general colors of ordinary significance are used.

The photographs and descriptions were taken during the winter season in Asle, District Satara, Maharashtra State, India when outdoor day temperature was 25° C. to 30° C. and cool nights, usually of 10° C. to 15° C. The age of the plant described is 3-4 months from rooted liners.

Botanical classification: *Sansevieria trifasciata* 'HANSOTI59'.

General information:

*Parentage.*—*Sansevieria trifasciata* 'Black Moon', unpatented.

*Optimal growth conditions.*—

*Light intensities.*—High adaptability to outdoor or indoor conditions.

*Temperature.*—Day: 25° C. to 35° C. Night: 15° C. to 25° C.

*Temperature tolerance.*—Tolerant to a low temperature of about 6° C. and a high temperature of 38° C. and above-very heat tolerant.

*Fertilization.*—Constant feed of 100 ppm N, 30 ppm P and 100 ppm K is used along with micronutrients with occasional leaching.

*Growth regulators.*—Not necessary for growth, however rooting hormone aids in rapid and prolific rooting of offsets.

Propagation:

*Typical.*—Vegetative, by side suckers which consistently come true to type. Does not come true from leaf cuttings.

*Rooting habit and description.*—Rhizomes are elongated, fleshy, giving rise to offsets (side shoots). Offsets root easily with fibrous adventitious roots from cut end. Rooting hormone helps in faster and more prolific rooting. Colored cream to brown, not accurately measured with R.H.S. chart.

*Time to initiate roots.*—20 to 25 days at 25° C. to 30° C.

*Time to produce a rooted liner.*—About 35 to 45 days at 25° C. to 30° C.

*Time to produce ready* 12 *cm potted plant from liner.*—About 12 to 15 weeks at 25° C. to 30° C.

Plant:

*General appearance and form.*—Monocot; leaf bases arranged in a rosette around growth point.

*Height.*—About 20 to 25 cm when grown in 12 cm pots.

*Spread.*—About 25 to 30 cm when grown when grown in a 12 cm size container.

*Growth rate and habit.*—About 1 cm per week; upright.

*Shape.*—Inverted triangle.

*Fragrance.*—None.

*Stem.*—Modified (rhizomes with erect foliage).

*Rosette height.*—About 20 to 25 cm height from top of pot when grown in 12 cm size container.

*Rosette diameter.*—About 25 to 30 cm.

*Strength.*—Strong and durable.

*Internode length.*—About 1 to 2 mm.

Foliage:

*Quantity.*—7 to 9 at approximately 3 to 4 months, 8 to 10 at approximately 6 months.

*Arrangement and attachment.*—Single, alternate; leaf bases arranged in a rosette around central growth point.

*Leaf length.*—About 22 to 27 cm.

*Leaf width.*—About 4 to 5 cm.

*Overall shape of leaf.*—Lanceolate.

*Apex shape.*—Acute, triangular and aristate, with soft tip.

*Base shape.*—Plane.

*Margin.*—Sharp, smooth.

*Texture.*—Upper Surface: Smooth and waxy texture.

*Texture.*—Under Surface: Smooth and waxy texture.

*Pubescence.*—None.

*Color.*—

*Upper surface around* 3-4 *months.*—Greyed-Green 189B tinted White 155A. Striations N189B. Marginal band near N144D.

*Lower surface around* 3-4 *months.*—Greyed-Green 191C and 191D with a background color of Yellow 2C. Striations N189B. Marginal band near N144D.

*Upper surface around* 4-5 *months.*—Greyed-Green 189B. Striations N189B. Lower $1/3^{rd}$ to ½ of the leaf suffused Yellow-Green 145A. Marginal band near N144D.

*Lower surface around* 4-5 *months.*—Greyed-Green 191C and 191D with a background color of Yellow 2C. Striations N189B. Lower ⅓rd to ½ of the leaf suffused Yellow-Green 145A. Marginal band near N144D.

*Upper surface around* 6-7 *months*.—Greyed-Green 189A. Striations N189B and N189C. Lower ⅓rd to ½ of the leaf suffused Green-Yellow 1B. Border 2 to 10 mm, bright green 136A. Yellow vertical striping next to green border near 2B and 2C. Basal blotch (medium in size) Green 135B.

*Crossbanding*.—Practically not discernable.

*Lower surface around* 6 *months*.—Greyed-Green 189A. Striations N189B and N189C. Lower ⅓rd to ½ of the leaf suffused Green-Yellow 1B. Border 2 to 10 mm, bright green 136A. Yellow vertical striping next to green border near 2B and 2C.

*Crossbanding*.—Practically not discernable.

*Upper surface* 2 *years*.—Mainly Yellow 2B and 2C. Center of leaf streaked Greyed-Green 189A and Green 136A. Border 5 to 10 mm, bright green 136A. Faint basal blotch (small to medium in size) Green 135A.

*Lower surface around* 2 *years*.—Mainly Yellow 2B and 2C. Center of leaf streaked Greyed-Green 189A and Green 136A. Border 5 to 10 mm, bright green 136A.

*Crossbanding*.—Practically not discernable.

*Venation pattern*.—Longitudinal/parallel leaf shape.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Occasionally shows Anthracnose and leaf spots but largely disease-free from clean mother stock and appropriate disease mitigation measures undertaken.

*Fruit/seed production*.—No fruits/seeds detected to date.

What is claimed is:

1. A new and distinct cultivar of *Sansevieria* plant named 'HANSOTI59' as herein illustrated and described.

* * * * *